United States Patent [19]

Schurter et al.

[11] Patent Number: 4,637,829
[45] Date of Patent: Jan. 20, 1987

[54] SULFONYLUREAS

[75] Inventors: Rolf Schurter, Binningen, Switzerland; Georg Pissiotas, Lörrach, Fed. Rep. of Germany

[73] Assignee: Ciba-Geigy Corporation, Ardsley, N.Y.

[21] Appl. No.: 723,233

[22] Filed: Apr. 15, 1985

[30] Foreign Application Priority Data

Apr. 27, 1984 [CH] Switzerland .......................... 2062/84

[51] Int. Cl.$^4$ .................. C07D 239/69; C07D 239/42; A01N 43/66; A01N 43/54
[52] U.S. Cl. ............................................ 71/90; 71/92; 71/93; 544/321; 544/324; 544/327; 544/331; 544/212
[58] Field of Search ...................... 71/92, 90; 544/321, 544/324, 327, 331

[56] References Cited

U.S. PATENT DOCUMENTS 4,460,401 7/1984 Sauers ................................ 544/212
4,518,776 5/1985 Meyer et al. ........................ 544/206

FOREIGN PATENT DOCUMENTS 44807 7/1981 European Pat. Off. .
44808 7/1981 European Pat. Off. .
51465 10/1981 European Pat. Off. .
85476 1/1983 European Pat. Off. .
2112784 7/1983 United Kingdom ................ 544/212

Primary Examiner—John M. Ford

Attorney, Agent, or Firm—Edward McC. Roberts; Kevin T. Mansfield

[57] ABSTRACT

N-(2-Heterocyclylphenylsulfonyl)-N'-pyrimidinylureas and N-(2-heterocyclylphenylsulfonyl)-N'-triazinylureas of the general formula I

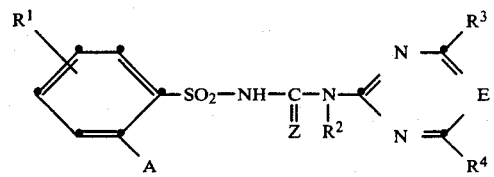

and the salts thereof with amines, alkali metal bases or alkaline earth metal bases or with quaternary ammonium bases have good pre-and postemergence selective herbicidal and growth regulating properties.

In this formula
A is a substituted furyl, thienyl or pyrrole radical,
E is nitrogen or the methine group —CH=,
Z is oxygen or sulfur,
$R^1$ is customary phenyl substituent,
$R^2$ is hydrogen, lower alkyl or lower alkoxy,
$R^3$ and $R^4$ are each independently hydrogen, lower alkyl, lower alkoxy, lower alkylthio, cycloalkyl, halogen, haloalkyl, haloalkoxy, haloalkylthio, alkoxyalkyl, dialkoxyalkyl, amino, diethylamino.

10 Claims, No Drawings

SULFONYLUREAS

The present invention relates to novel N-(2-heterocyclylphenylsulfonyl)-N'-pyrimidinylureas and N-(2-heterocyclylphenylsulfonyl)-N'-triazinylureas with herbicidal and plant growth regulating properties, to the preparation thereof, to compositions containing them as active ingredients, and to methods of using them for controlling weeds, preferably selectively, in crops of useful plants, or for regulating and inhibiting plant growth. Moreover, the invention also relates to novel 2-heterocyclylphenylsulfonylisocyanates, 2-heterocyclylphenylsulfonylisothiocyanates, 2-heterocyclylphenylsulfonylcarbamates and 2-heterocyclylphenylsulfonamides prepared as intermediates.

The invention relates to N-(2-heterocyclylphenylsulfonyl)-N'-pyrimidinylureas and N-(2-heterocyclylphenylsulfonyl)-N'-triazinylureas of the general formula I

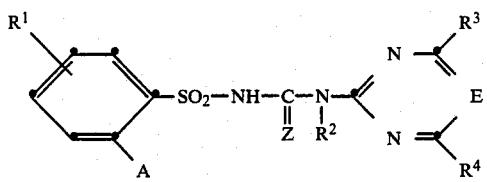

wherein
A is a

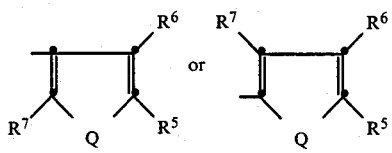

radical,
E is nitrogen or the methine group $-CH=$,
Q is oxygen, sulfur or the imino group $-NR^8=$,
Z is oxygen or sulfur,
$R^1$ is hydrogen, halogen, nitro, $C_1$-$C_4$alkyl, $C_1$-$C_4$haloalkyl, $C_1$-$C_4$-alkoxy, $C_1$-$C_4$haloalkoxy, $C_1$-$C_4$alkoxycarbonyl, $C_1$-$C_4$alkylthio, $C_1$-$C_4$alkylsulfinyl, $C_1$-$C_4$alkylsulfonyl or $C_2$-$C_5$alkoxyalkoxy,
$R^2$ is hydrogen, $C_1$-$C_4$alkyl or $C_1$-$C_3$alkoxy,
$R^3$ and $R^4$ are each independently hydrogen, halogen, $C_1$-$C_4$alkyl, $C_1$-$C_4$haloalkyl, $C_3$-$C_5$cycloalkyl, $C_1$-$C_4$alkoxy, $C_1$-$C_4$haloalkoxy, $C_1$-$C_4$alkylthio, $C_1$-$C_4$haloalkylthio, $C_2$-$C_5$alkoxyalkyl, $C_3$-$C_6$dialkoxyalkyl or an amino group $-NR^{16}R^{17}$,
$R^5$ is a $C_1$-$C_6$alkyl radical which is substituted by hydroxy, $C_1$-$C_4$alkylthio, cyano or a $-COOR^{12}$ group or $-NR^{13}R^{14}$, or is $C_2$-$C_6$alkoxyalkoxy or $C_1$-$C_4$haloalkoxy, $C_2$-$C_6$haloalkenyl, or a phenyl, benzyl, phenoxy or phenylthio radical which is unsubstituted or substituted by $C_1$-$C_3$alkyl, $C_1$-$C_3$alkoxy or halogen, or $R^5$ is one of the groupings selected from $-COOR^9$, $-COR^{10}$, $-C(R^{10})=NOR^{11}$, $-CH=CH-COOR^{12}$, $-CH=C(COOR^{12})_2$, $-CH=C(CN)COOR^{12}$, $-CR^{10}(OR^{14})_2$,

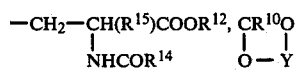

or $-NR^{13}-COR^{14}$,
$R^6$ and $R^7$ are each independently hydrogen, halogen, $C_1$-$C_6$alkyl, $C_1$-$C_6$haloalkyl, $C_2$-$C_6$alkoxyalkyl, $C_1$-$C_6$alkoxy, $C_1$-$C_4$alkylthio, di($C_1$-$C_4$alkyl)amino, cyano, nitro, methoxycarbonyl or the same as $R^5$,
$R^8$ is hydrogen, $C_1$-$C_6$alkyl, $C_3$-$C_6$cycloalkyl, benzyl, phenyl or a $-COOR^{12}$ radical
$R^9$ is a $C_2$-$C_6$alkyl radical which is unsubstituted or substituted by halogen, $C_1$-$C_4$alkoxy or phenyl, or is $C_3$-$C_6$alkenyl or $C_3$-$C_6$alkynyl,
$R^{10}$ is hydrogen, $C_1$-$C_6$alkyl which is unsubstituted or substituted by $C_1$-$C_4$alkoxy or phenoxy which may in turn be substituted by halogen, $C_1$-$C_3$alkyl or $C_1$-$C_3$alkoxy, or $R^{10}$ is $C_2$-$C_4$alkenyl,
$R^{11}$ is hydrogen or $C_1$-$C_6$alkyl which is unsubstituted or substituted by cyano or $-COOR^{12}$,
$R^{12}$ is hydrogen, methyl, halomethyl, methoxymethyl, benzyl or the same as $R^9$,
$R^{13}$ and $R^{14}$ are each independently hydrogen, $C_1$-$C_6$alkyl or $C_3$-$C_6$alkenyl,
$R^{15}$ is $C_1$-$C_6$alkyl or a $-COOR^{12}$ radical,
$R^{16}$ and $R^{17}$ are each independently hydrogen or $C$-$C_4$alkyl, and
Y is a $C_2$-$C_8$alkylene group,
and to the salts thereof with organic or inorganic bases.

Ureas, triazines and pyrimidines with herbicidal properties are generally known in the art. N-(Heterocyclylaminocarbonyl)arylsulfonamides with herbicidal and plant growth regulating properties have recently been described, for example in U.S. Pat. No. 4,127,405 and in European patent applications 44 807, 44 808, 51,465 and 85 476.

In the above definitions, alkyl denotes straight chain or branched alkyl, e.g. methyl, ethyl, n-propyl, isopropyl or the four butyl isomers. Cycloalkyl radicals are e.g. cyclopropyl, cyclobutyl and cyclopentyl which may also be substituted by methyl.

Alkoxy denotes methoxy, ethoxy, n-propyloxy, isopropyloxy, the four butyloxy isomers, n-amyloxy, isoamyloxy, 2-amyloxy or 3-amyloxy, with methoxy, ethoxy or isopropoxy being preferred.

Alkylthio is e.g. methylthio, ethylthio, n-propylthio, isopropylthio, n-butylthio or n-pentylthio, with methylthio and ethylthio being preferred.

In these definitions, halogen by itself or as moiety of haloalkoxy is fluorine, chlorine, bromine and iodine, with fluorine and chlorine being preferred.

The invention also comprises the salts which the compounds of formula I are able to form with amines, alkali metal bases and alkaline earth metal bases, or with quaternary ammonium bases. Preferred salt-forming alkali metal hydroxides and alkaline earth metal hydroxides are the hydroxides of lithium, sodium, potassium, magnesium or calcium, most preferably those of sodium or potassium.

Examples of suitable salt-forming amines are primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline. Preferred amines are ethylamine, propylamine, diethylamine or triethylamine, with isopropylamine and diethanolamine being most preferred.

Examples of quaternary ammonium bases are, in general, the cations of haloammonium salts, e.g. the tetramethylammonium cation, the trimethylbenzylammonium cation, the triethylbenzylammonium cation, the tetraethylammonium cation, the trimethylethylammonium cation, and also the ammonium cation.

Radicals represented by A are furyl, thienyl and pyrrole derivatives which are bonded in the 2- or 3-position and which may be additionally substituted by $R^5$, $R^6$, $R^7$, or, in the case of pyrrole, also by $R^8$.

Among the sulfonylureas of formula I, those compounds are particularly effective which are of formula Ia

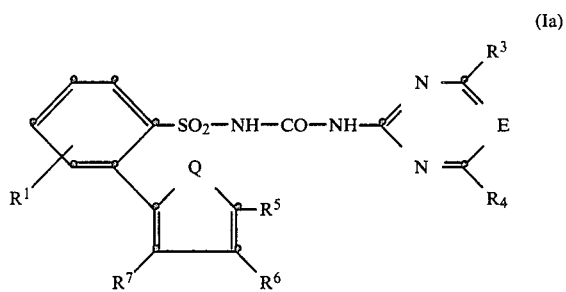

wherein E, Q, $R^1$, $R^3$, $R^4$, $R^5$, $R^6$ and $R^7$ are as defined for formula I, most particularly those compounds wherein Q is oxygen or sulfur, $R^1$ is hydrogen or halogen, $R^3$ is methyl, methoxy, ethoxy, chlorine, methoxymethyl, dimethoxymethyl, $C_1$-$C_2$haloalkoxy or dimethylamino, $R^4$ is methyl, methoxy, ethoxy, cyclopropyl or $OCHF_2$, and E and $R^5$, $R^6$ and $R^7$ are as defined for formula I.

Particularly interesting compounds are those of formula Ib

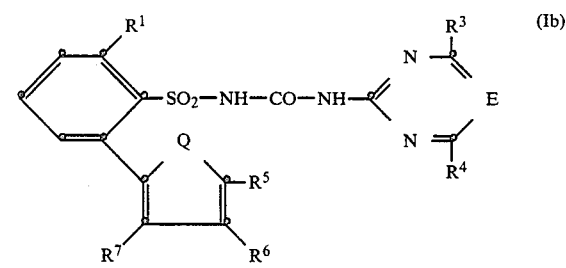

wherein

Q is oxygen or sulfur, $R^1$ is hydrogen or chlorine, $R_3$ and $R^4$ are each independently methyl or methoxy, and E, $R^5$, $R^6$ and $R^7$ are as defined for formula I, especially N-[2-(5-acetylfuran-2-yl)phenylsulfonyl]-N'-(4,6-dimethoxypyrimidin-2-yl)urea and N-[2-(5-acetylfuran-2-yl)phenylsulfonyl]-N'-(4-methoxy-6-methylpyrimidin-2-yl)urea.

Further particularly interesting compounds are sulfonylureas of formula Ic

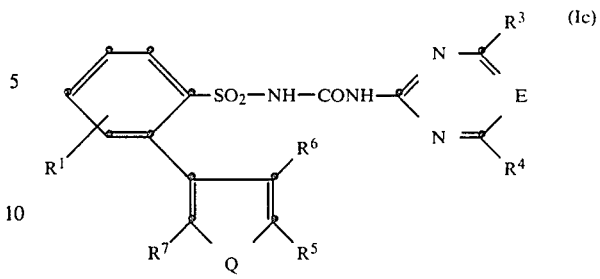

wherein E, Q, $R^1$, $R^3$, $R^4$, $R^5$, $R^6$ and $R^7$ are as defined for formula I, most particularly those compounds wherein Q is oxygen or sulfur, $R^1$ is hydrogen or halogen, $R^3$ is methyl, methoxy, ethoxy, chlorine, methoxymethyl, dimethoxymethyl, $C_1$-$C_2$haloalkoxy or dimethylamino, $R^4$ is methyl, methoxy, ethoxy, cyclopropyl or $OCF_2$, and E, $R^5$, $R^6$ and $R^7$ are as defined for formula I.

Compounds also having good activity are of formula Id

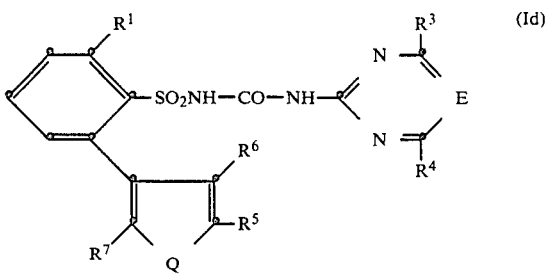

wherein

Q is oxygen or sulfur, $R^1$ is hydrogen or chlorine, $R^3$ and $R^4$ are each independently methyl or methoxy, and E, $R^5$, $R^6$ and $R^7$ are as defined for formula I, especially N-[2-(5-acetylfuran-2-methyl-3-yl)phenylsulfonyl]-N'-(4,6-dimethoxypyrimidin-2-yl)urea and N-[2-(5-acetylfuran-2-methyl-3-yl)phenylsulfonyl]-N'-(4-methoxy-6-methylpyrimidin-2-yl)urea.

The preparation of the compounds of formula I is effected in an inert organic solvent.

In accordance with a first process, the compounds of formula I are obtained by reacting a 2-heterocyclylphenylsulfonamide of formula II

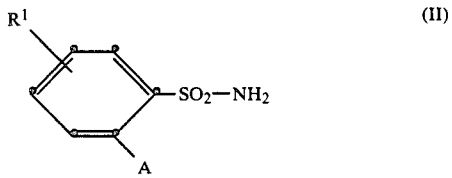

wherein $R^1$ and A are as defined for formula I, with an N-pyrimidinylcarbamate or N-triazinylcarbamate of formula III

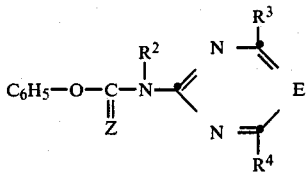

(III)

wherein E, $R^2$, $R^3$, $R^4$ and Z are as defined for formula I, optionally in the presence of a base.

In accordance with a second process, compounds of formula I are obtained by reacting a 2-heterocyclyl-phenylsulfonylisocyanate or 2-heterocyclylphenylsul-fonylisothiocyanate of formula IV

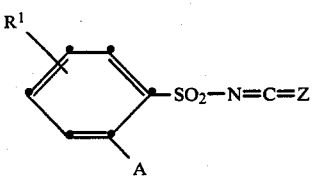

(IV)

wherein A, $R^1$ and Z are as defined for formula I, with an aminopyrimidine or aminotriazine of formula V

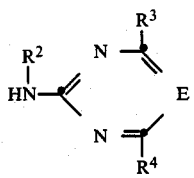

(V)

wherein E, $R^2$, $R^3$ and $R^4$ are as defined for formula I, optionally in the presence of a base.

Finally, the compounds of formula I can also be obtained by reacting a 2-heterocyclylphenylsulfonylcar-bamate of formula VI

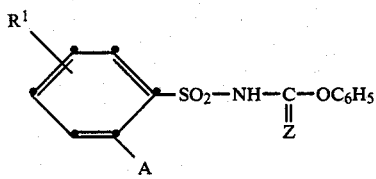

(VI)

wherein A, $R^1$ and Z are as defined for formula I, with an aminopyrimidine or aminotriazine of formula V above.

If desired, the resultant ureas of formula I can be converted into addition salts with amines, alkali metal hydroxides or alkaline earth metal hydroxides or with quaternary ammonium bases. This is accomplished e.g. by reaction with the equimolar amount of base and by evaporating off the solvent.

The starting materials of formula II, IV and VI are novel and can be prepared in accordance with the following methods:

The novel substituted phenylsulfonamides of formula II employed as intermediates are obtained e.g. from the corresponding aniline derivatives by diazotisation and replacement of the diazo group with sulfur dioxide, in the presence of a catalyst such as copper(I) chloride in hydrochloric acid or acetic acid, and reacting the resultant substituted phenylsulfonyl chloride with ammonia.

Corresponding aniline derivatives are known or can be prepared by known methods.

The intermediates of formulae II, IV and VI are novel. They have been specially developed for the synthesis of compounds of formula I and therefore constitute a further object of the present invention.

The substituted phenylsulfonylisocyanates of formula IV can be obtained e.g. by phosgenating the sulfonamides of formula II, in the presence of butyl isocyanate and in an inert organic solvent, at reflux temperature. Similar preparatory methods are described in "Neuere Methoden der präparativen organischen Chemie", Band VI, 211–229, Verlag Chemie, Weinheim, 1970.

The substituted isothiocyanates of formula IV are obtained by treating the sulfonamides of formula II with carbon disulfide and potassium hydroxide and subsequently phosgenating the dipotassium salt. Such processes are described in Arch. Pharm. 229, 174 (1966).

The substituted phenylsulfonylcarbamates of formula VI are obtained by reacting the sulfonamides of formula II with diphenyl carbonate or phenyl chloroformate or sulfur analogues thereof, in the presence of a base. Similar processes are described in Japanese patent specification 61 169.

The starting aminopyrimidines and aminotriazines of formula V and corresponding phenylcarbamates of formula III have either long been known or they are disclosed in Swiss patent application 3527/82-8 or they can be obtained by known methods from compounds disclosed therein.

It is convenient to carry out these reactions for obtaining compounds of formula I in aprotic, inert organic solvents or solvent mixtures. Examples of such solvents are ethers such as dioxane, diethyl ether, tetrahydrofuran, ethylene glycol dimethyl ether, diethylene glycol dimethyl ether; hydrocarbons such as benzene, toluene, xylene, cyclohexane; nitriles such as acetonitrile, propionitrile; chlorinated hydrocarbons such as methylene chloride, chloroform, carbon tetrachloride, chlorobenzene or diemthylsulfoxide. The reaction temperatures are preferably in the range from −20° C. to +120° C. The reactions are normally slightly exothermic and can be carried out at room temperature. To shorten the reaction time or also to initiate the reaction, it is expedient to heat the reaction mixture briefly. The reaction time can also be shortened by addition of a base as catalyst.

Suitable bases may be both organic, e.g. trimethylamine, triethylamine, quinuclidine, 1,4-diazabicyclo[2.2.2]octane, 1,8-diazabicyclo[5.4.0]undec-7-ene etc., and inorganic, e.g. hydrides such as sodium hydride or calcium hydride, hydroxides such as sodium hydroxide or potassium hydroxide, carbonates such as sodium carbonate or potassium carbonate, or bicarbonates such as potassium bicarbonate or sodium bicarbonate.

The final products can be isolated by concentrating the solvent and purified by recrystallising or triturating the solid residue in solvents in which they are not readily soluble, e.g. an ether or an aromatic hydrocarbon.

The compounds of formula I are stable compounds and no precautionary measures are required for handling them.

When used at low rates of application, the compounds of formula I have good selective growth inhibiting and selective herbicidal properties which make them most suitable for use in crops of useful plants, preferably in cereals, cotton, soybeans, maize and rice. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced growth regulating, especially growth inhibiting, properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth regulators resides in the fact that nutrients are able increasingly to promote flower formation and fruiting, whereas vegetative growth is inhibited.

At higher rates of application of compounds of formula I, all tested plants are so severely damaged in their development that they die.

The invention also relates to herbicidal and growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of applications, such as spraying, atomising, dusting, scattering or pouring, are chosen in accordance with the intended objectives and the prevailing circumstances.

The formulations, i.e., the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkali earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzene sulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyl-trimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J., 1981; H. Stache, "Tensid-Taschenbuch", 2nd Edition, C. Hanser Verlag, Munich & Vienna, 1981; M. and J. Ash, "Encyclopedia of Surfactants", Vol. I–III, Chemical Publishing Co., New York, 1980–81.

The compositions usually contain 0.1 to 95%, preferably 0.1 to 80%, of a compound of formula I, 1 to 99.9%, of a solid or liquid adjuvant, and 0 to 25%, preferably 0.1 to 25%, of a surfactant.

Preferred formulations are composed in particular of the following constituents (%=percentage by weight):

| Emulsifiable concentrates | | |
|---|---|---|
| active ingredient: | 1 to 20%, | preferably 5 to 10% |
| surfactant: | 5 to 30%, | preferably 10 to 20% |
| liquid carrier: | 50 to 94%, | preferably 70 to 85% |
| Dusts | | |
| active ingredient: | 0.1 to 10%, | preferably 0.1 to 1% |
| solid carrier: | 99.9 to 90%, | preferably 99.9 to 99% |
| Suspension concentrates | | |
| active ingredient: | 5 to 75%, | preferably 10 to 50% |
| water: | 94 to 25%, | preferably 90 to 30% |
| surfactant: | 1 to 40%, | preferably 2 to 30% |
| Wettable powders | | |
| active ingredient: | 0.5 to 90%, | preferably 1 to 80% |
| surfactant: | 0.5 to 20%, | preferably 1 to 15% |
| solid carrier: | 5 to 95%, | preferably 15 to 90% |
| Granulates | | |
| active ingredient: | 0.5 to 30%, | preferably 3 to 15% |
| solid carrier: | 99.5 to 70%, | preferably 97 to 85%. |

Whereas commercial products will be preferably formulated as concentrates, the end user will normally employ dilute formulations. The formulations can be diluted to a concentration as low as 0.001% of active ingredient.

The compositions may also contain further ingredients such as stabilisers, antifoams, viscosity regulators, binders, tackifiers, as well as fertilisers and other compounds for obtaining special effects.

Such formulations constitute an object of this invention.

The following non-limitative Example serves to illustrate the invention in more detail.

EXAMPLE 1

Preparation of N-[2-(5-acetylfuran-2-yl)phenylsulfonyl]-N'-(4,6-dimethoxypyrimidin-2-yl)urea

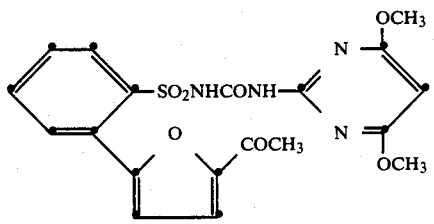

2.15 g (0.008 .mol) of 2-(5-acetylfuranyl-2-yl)phenylsulfonamide and 2.20 g of 4,6-dimethoxy-2-phenoxycarbonylaminopyrimidine are suspended in 40 ml of acetonitrile. 1.25 ml of 1,8-diazabicyclo[5.4.0]undec-7-ene in 5 ml of acetonitrile are then slowly added dropwise to the suspension, whereupon a solution gradually forms. The reaction mixture is stirred for 3 hours at room temperature and then poured into ice/water and 0.5 ml of methanesulfonic acid is added. The mixture is stirred for 30 minutes, the resultant precipitate is filtered off, washed with water and diethyl ether and dried, affording 3.5 g (98% of theory) of the above urea with a melting point of 199°–200° C.

The following ureas are prepared in a manner analogous to that of this Example.

TABLE 1

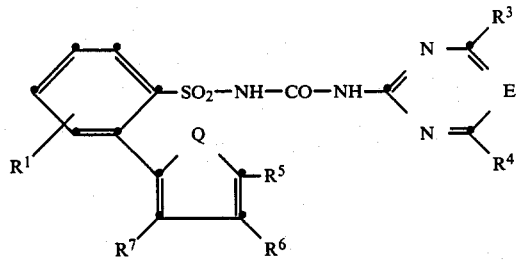

| Comp. | Q | R¹ | R⁵ | R⁶ | R⁷ | E | R³ | R⁴ | m.p. [°C.] |
|---|---|---|---|---|---|---|---|---|---|
| 1.01 | O | H | COCH₃ | H | H | CH | OCH₃ | OCH₃ | 199–200 decomp. |
| 1.02 | O | H | COCH₃ | H | H | CH | OCH₃ | CH₃ | 213–215 decomp. |
| 1.03 | O | H | COCH₃ | H | H | N | OCH₃ | OCH₃ | |

TABLE 1-continued

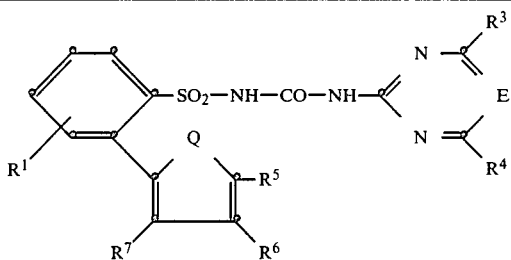

| Comp. | Q | R¹ | R⁵ | R⁶ | R⁷ | E | R³ | R⁴ | m.p. [°C.] |
|---|---|---|---|---|---|---|---|---|---|
| 1.04 | O | H | COCH₃ | H | H | N | OCH₃ | CH₃ | |
| 1.05 | S | H | COCH₃ | H | H | CH | OCH₃ | OCH₃ | |
| 1.06 | S | H | COCH₃ | H | H | N | OCH₃ | OCH₃ | |
| 1.07 | O | —Cl | COCH₃ | H | H | N | OCH₃ | OCH₃ | |
| 1.08 | O | H | CH₂SCH₃ | H | H | CH | OCH₃ | OCH₃ | |
| 1.09 | O | H | CH₂SCH₃ | H | H | N | OCH₃ | OCH₃ | |
| 1.10 | O | H | COOC₂H₅ | H | H | CH | OCH₃ | OCH₃ | |
| 1.11 | O | H | COOC₂H₅ | H | H | N | OCH₃ | OCH₃ | |
| 1.12 | S | H | COOC₂H₅ | H | H | CH | OCH₃ | OCH₃ | |
| 1.13 | O | H | —C(CH₃)=NOCH₃ | H | H | CH | OCH₃ | OCH₃ | |
| 1.14 | O | H | —C(CH₃)=NOCH₃ | H | H | N | OCH₃ | OCH₃ | |
| 1.15 | O | H | —C(CH₃)=NOCH₂CN | H | H | CH | OCH₃ | OCH₃ | |
| 1.16 | O | H | —CH=CH—COOCH₃ | H | H | CH | OCH₃ | OCH₃ | |
| 1.17 | S | H | —CH=CH—COOCH₃ | H | H | CH | OCH₃ | OCH₃ | |
| 1.18 | O | H | —CH₂CN | H | H | N | OCH₃ | OCH₃ | |
| 1.19 | O | H | —CH₂COOC₂H₅ | H | H | CH | OCH₃ | OCH₃ | |
| 1.20 | S | H | —CH₂COOCH₃ | H | H | CH | OCH₃ | OCH₃ | |
| 1.21 | O | H | —CH₂N(CH₃)₂ | H | H | CH | OCH₃ | OCH₃ | |
| 1.22 | O | H | H | COOCH₃ | H | CH | OCH₃ | OCH₃ | |
| 1.23 | O | H | CH₃ | COOC₂H₅ | CH₃ | CH | OCH₃ | OCH₃ | |
| 1.24 | O | H | 2-methyl-1,3-dioxolan-2-yl | H | H | CH | OCH₃ | OCH₃ | |
| 1.25 | O | H | 2-methyl-1,3-dioxolan-2-yl | H | H | N | OCH₃ | OCH₃ | |
| 1.26 | O | H | 1,3-dioxolan-2-yl | H | H | CH | OCH₃ | OCH₃ | |
| 1.27 | O | H | CHO | H | H | CH | OCH₃ | OCH₃ | 179 decomp. |
| 1.28 | O | H | CHO | H | H | CH | CH₃ | OCH₃ | 171 decomp. |
| 1.29 | O | H | CHO | H | H | N | CH₃ | OCH₃ | 175 decomp. |
| 1.30 | O | H | —CH₂CN | H | H | CH | OCH₃ | OCH₃ | 190–193 |

TABLE 2

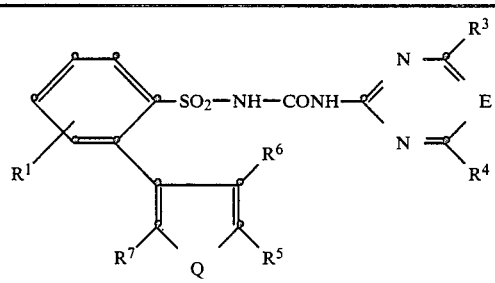

| Comp. | Q | R¹ | R⁵ | R⁶ | R⁷ | E | R³ | R⁴ | m.p. [°C.] |
|---|---|---|---|---|---|---|---|---|---|
| 2.01 | S | H | COCH₃ | H | CH₃ | CH | OCH₃ | CH₃ | |
| 2.02 | S | H | COCH₃ | H | CH₃ | CH | OCH₃ | OCH₃ | |
| 2.03 | S | H | COCH₃ | H | CH₃ | N | OCH₃ | OCH₃ | |
| 2.04 | O | H | COCH₃ | H | CH₃ | CH | OCH₃ | OCH₃ | |
| 2.05 | O | H | COCH₃ | H | CH₃ | N | OCH₃ | OCH₃ | |
| 2.06 | O | 6-Cl | COCH₃ | H | CH₃ | CH | OCH₃ | OCH₃ | |
| 2.07 | S | 6-Cl | COCH₃ | H | CH₃ | N | OCH₃ | OCH₃ | |
| 2.08 | O | H | COCH₃ | CH₃ | CH₃ | CH | OCH₃ | OCH₃ | |
| 2.09 | O | H | COCH₃ | CH₃ | CH₃ | N | OCH₃ | OCH₃ | |
| 2.10 | O | H | COOC₂H₅ | H | CH₃ | CH | OCH₃ | OCH₃ | |
| 2.11 | O | 6-Cl | COOC₂H₅ | H | CH₃ | N | OCH₃ | OCH₃ | |
| 2.12 | S | H | COOC₂H₅ | H | CH₃ | CH | OCH₃ | OCH₃ | |

Intermediates:

TABLE 3

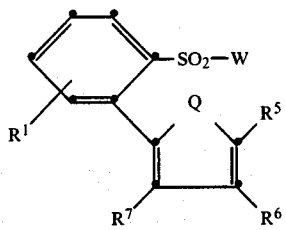

| Comp. | Q | R¹ | R⁵ | R⁶ | R⁷ | W | Physical data |
|---|---|---|---|---|---|---|---|
| 3.01 | O | H | —COCH₃ | H | H | —NH₂ | m.p. 183–186° C. |
| 3.02 | S | H | —COCH₃ | H | H | —NH₂ | |
| 3.03 | O | 6-Cl | —COCH₃ | H | H | —NH₂ | |
| 3.04 | S | 6-Cl | —COCH₃ | H | H | —NH₂ | |
| 3.05 | O | H | —CH₂SCH₃ | H | H | —NH₂ | |
| 3.06 | O | 6-Cl | —CH₂SCH₃ | H | H | —NH₂ | |
| 3.07 | S | H | —CH₂SCH₃ | H | H | —NH₂ | |
| 3.08 | O | H | —COOC₂H₅ | H | H | —NH₂ | |
| 3.09 | O | H | —COOC₂H₅ | H | H | —NHCOOC₆H₅ | |
| 3.10 | O | H | —C(CH₃)=NOCH₃ | H | H | —NH₂ | |
| 3.11 | O | H | —C(CH₃)=NOCH₂CN | H | H | —NH₂ | |
| 3.12 | O | H | —CH=CH—COOCH₃ | H | H | —NH₂ | |
| 3.13 | S | H | —CH=CH—COOCH₃ | H | H | —NH₂ | |
| 3.14 | O | H | —CH₂—CN | H | H | —NH₂ | m.p. 155° C. |
| 3.15 | O | H | —CH₂COOC₂H₅ | H | H | —NH₂ | |
| 3.16 | S | H | —CH₂COOCH₃ | H | H | —NH₂ | |
| 3.17 | O | H | —CH₂—N(CH₃)₂ | H | H | NH₂ | |
| 3.18 | O | H | —CH=C(COOCH₃)₂ | H | H | NH₂ | |
| 3.19 | O | H | —N(CH₃)COCH₃ | H | H | NH₂ | |
| 3.20 | O | H | —CH=C(CN)COOCH₃ | H | H | NH₂ | |
| 3.21 | S | H | —COOC₂H₅ | H | H | NCO | |
| 3.22 | O | H | H | COOCH₃ | H | NH₂ | |
| 3.23 | NH | H | CH₂COOC₂H₅ | H | H | NH₂ | |
| 3.24 | O | H | CH₃ | COOC₂H₅ | CH₃ | NH₂ | |
| 3.25 | O | H | CH₂COOCH₃ | H | H | Cl | |
| 3.26 | S | H | CH₂COOCH₃ | H | H | Cl | |
| 3.27 | O | H | CH₃ | COOC₂H₅ | CH₃ | Cl | |
| 3.28 | O | H | CHO | H | H | NH₂ | m.p. 110–115° C. |
| 3.29 | O | H | 2-methyl-1,3-dioxolan-2-yl | H | H | NH₂ | |

TABLE 4

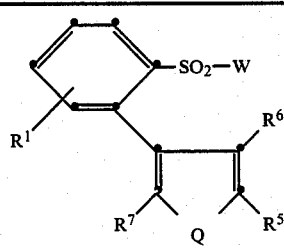

| Comp. | Q | R¹ | R⁵ | R⁶ | R⁷ | W | Physical data |
|---|---|---|---|---|---|---|---|
| 4.01 | S | H | —COCH₃ | H | CH₃ | NH₂ | |
| 4.02 | O | H | —COCH₃ | H | CH₃ | NH₂ | |
| 4.03 | S | 6-Cl | —COCH₃ | H | CH₃ | NH₂ | |
| 4.04 | O | 6-Cl | —COOC₂H₅ | H | CH₃ | NH₂ | |
| 4.05 | O | H | —COCH₃ | CH₃ | CH₃ | NH₂ | |
| 4.06 | O | H | —COOC₂H₅ | H | OCH₃ | NH₂ | |

FORMULATION EXAMPLES

EXAMPLE 3

Formulation Examples for liquid active ingredients of formula I (throughout, percentages are by weight)

| (a) Emulsifiable concentrates | (a) | (b) | (c) |
|---|---|---|---|
| a compound of formula I | 20% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| (b) Solutions | (a) | (b) | (c) | (d) |
|---|---|---|---|---|
| a compound of formula I | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum distillate (boiling range 160–190°) | — | — | 94% | — |

These solutions are suitable for application in the form of microdrops.

| (c) Granulates | (a) | (b) |
|---|---|---|
| a compound of formula I | 5% | 10% |
| kaolin | 94% | — |
| highly dispersed silicic acid | 1% | — |

-continued

| (c) Granulates | (a) | (b) |
|---|---|---|
| attapulgite | — | 90% |

The active ingredient is dissolved in methylene chloride, the solution is sprayed onto the carrier, and the solvent is subsequently evaporated off in vacuo.

| (d) Dusts | (a) | (b) |
|---|---|---|
| a compound of formula I | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

EXAMPLE 4

Formulation examples for solid active ingredients of formula I (throughout, percentages are by weight)

| (a) Wettable powders | (a) | (b) |
|---|---|---|
| a compound of formula I | 20% | 60% |
| sodium lignosulfonate | 5% | 5% |
| sodium lauryl sulfate | 3% | — |
| sodium diisobutylnaphthalenesulfonate | — | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | |
|---|---|
| a compound of formula I | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| (c) Dusts | (a) | (b) |
|---|---|---|
| a compound of formula I | 5% | 8% |
| talcum | 95% | — |
| kaolin | — | 92% |

Ready-for-use dusts are obtained by mixing the active ingredient with the carriers, and grinding the mixture in a suitable mill.

| (d) Extruder granulate | |
|---|---|
| a compound of formula I | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| (e) Coated granulate | |
|---|---|
| a compound of formula I | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | |
|---|---|
| a compound of formula I | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLES

EXAMPLE 5

Preemergence herbicidal action

Plastic pots are filled with expanded vermiculite (density: 0.135 g/cm$^3$, water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: *Nasturtium officinalis, Agrostis tenuis, Stellaria media* and *Digitaria sanguinalis*. The pots are then kept in a climatic chamber at 20° C., an illumination of about 20 klux and a relative humidity of 70%. During the germinating phase of 4 to 5 days, the pots are covered with lightpermeable material and watered with deionised water to increase the local humidity. After the 5th day, 0.5% of a commercial liquid fertiliser is added to the water. The test is evaluated 12 days after sowing and the action on the plants is assessed according to the following rating:

1: plant has not germinated or it has died
1-3: very severe damage
4-5: severe damage, stunted growth
6: damage from which the plant is able to recuperate after subsidence of the phytotoxic acitivity
7-8: slight damage
9: plant as untreated controls The results are shown in Table 5.

TABLE 5

| | Compound: | | | | | |
|---|---|---|---|---|---|---|
| Plant: | 1.01 | 1.02 | 1.27 | 1.28 | 1.29 | 1.30 |
| Nasturtium | 2 | 2 | 1 | 1 | 1 | 1 |
| Agrostis | 2 | 2 | 1 | 1 | 1 | 1 |
| *Stellaria media* | 2 | 2 | 1 | 1 | 1 | 1 |

TABLE 5-continued

| Plant: | Compound: | | | | | |
|---|---|---|---|---|---|---|
| | 1.01 | 1.02 | 1.27 | 1.28 | 1.29 | 1.30 |
| Digitaria sanguinalis | 2 | 2 | 1 | 1 | 1 | 1 |

EXAMPLE 6

Growth inhibition of cereals

Summer barley (*Hordeum vulgare*) and summer rye (Secale) are sown in sterilised soil in plastic beakers in a greenhouse and watered as required. The cereal shoots are treated about 21 days after sowing with an aqueous spray mixture of a compound of the formula I. The concentration corresponds to up to 100 g of active ingredient per hectare. Evaluation of the growth of the cereals is made 21 days after application. A comparison with untreated controls shows that the new growth of cereal plants treated with compounds of formula I is reduced (60–90% of the controls) and that the diameter of the stalks has in some cases increased.

EXAMPLE 7

Growth inhibition of grasses

Seeds of the grasses *Lolium perenne, Poa pratensis, Festuca ovina, Dactylis glomerate* and *Cynodon dactylon* are sown in plastic dishes filled with an earth/peat/sand mixture (6:3:1), in a greenhouse, and watered as required. The emergent grasses are cut back weekly to a height of 4 cm, and about 50 days after sowing and 1 day after the last cut are sprayed with an aqueous spray mixture of a compound of formula I. The concentration of test compound corresponds to a rate of application of up to 100 g a.i. per hectare. The growth of the grasses is evaluated 21 days after application. The compounds of formula I effect a reduction in new growth in the range of 10–30% in comparison with untreated controls.

What is claimed is:

1. An N-(2-heterocyclylphenylsulfonyl)-N'-pyrimidinylurea of the formula

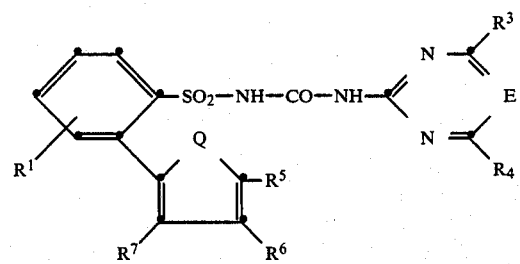

wherein
E is methine —CH=,
Q is oxygen or sulfur,
$R^1$ is hydrogen or chlorine,
$R^3$ and $R^4$ are each independently of the other methyl or methoxy,
$R_5$ is $C_1$-$C_6$alkyl substituted by cyano, —$COR^{10}$, —$C(R^{10})$=$NOR^{11}$, —CH=CH—$COOR^{12}$ or

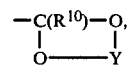

$R^6$ and $R^7$ are hydrogen,
$R^{10}$ is hydrogen, unsubstituted $C_1$-$C_{10}$alkyl or $C_2$-$C_4$alkenyl,
$R^{11}$ is unsubstituted $C_1$-$C_6$alkyl,
$R^{12}$ is methyl and
Y is $C_2$-$C_8$alkylene.

2. An N-(2-heterocyclylphenylsulfonyl)-N'-pyrimidinylurea according to claim 1 wherein
Q is oxygen,
$R_1$ is hydrogen,
$R_5$ is $C_1$-$C_6$alkyl substituted by cyano or —$COR^{10}$ and
$R^{10}$ is hydrogen or unsubstituted $C_1$-$C_{10}$alkyl.

3. N-[2-(5-Acetylfuran-2-yl)phenylsulfonyl]-N'-(4,6-dimethoxypyrimidin-2-yl)urea according to claim 1.

4. N-[2-(5-Acetylfuran-2-yl)phenylsulfonyl]-N'-(4-methoxy-6-methylpyrimidin-2-yl)urea according to claim 1.

5. A herbicidal and plant growth regulating composition which comprises, as active ingredient, a substituted N-phenylsulfonyl-N'-pyrimidinylurea claim 1, together with a carrier and/or other adjuvants.

6. A method of controlling undesired plant growth, which method comprises applying to the plants or to the locus thereof an effective amount of a compound of claim 1, or of a composition containing such a compound.

7. A method of inhibiting plant growth, which method comprises applying to the plants or to the locus thereof an effective amount of a compound of claim 1, or of a composition containing such a compound.

8. A method of influencing plant growth for increasing yield, which method comprises applying to the plants or to the locus thereof an effective amount of a compound of claim 1, or of a composition containing such a compound.

9. A method of selectively controlling weeds pre- or postemergence in crops of useful plants, which method comprises applying to the plants or to the locus thereof an effective amount of a compound of claim 1, or of a composition containing such a compound.

10. A method of suppressing plant growth beyond the 2-leaf stage preemergence, which method comprises applying to the plants or to the locus thereof an effective amount of a compound of claim 1, or of a composition containing such a compound.

* * * * *